(12) United States Patent
Shibuya

(10) Patent No.: US 12,298,232 B2
(45) Date of Patent: May 13, 2025

(54) ANALYSIS DEVICE, PROGRAM FOR ANALYSIS DEVICE, AND ANALYSIS METHOD

(71) Applicant: HORIBA, LTD., Kyoto (JP)

(72) Inventor: Kyoji Shibuya, Kyoto (JP)

(73) Assignee: Horiba, Ltd. (JP)

( * ) Notice: Subject to any disclaimer, the term of this patent is extended or adjusted under 35 U.S.C. 154(b) by 268 days.

(21) Appl. No.: 17/928,388

(22) PCT Filed: May 25, 2021

(86) PCT No.: PCT/JP2021/019833
§ 371 (c)(1),
(2) Date: Nov. 29, 2022

(87) PCT Pub. No.: WO2021/241589
PCT Pub. Date: Dec. 2, 2021

(65) Prior Publication Data
US 2023/0204498 A1 Jun. 29, 2023

(30) Foreign Application Priority Data
May 29, 2020 (JP) ................. 2020-094709

(51) Int. Cl.
 *G01N 21/31* (2006.01)
 *G01N 33/00* (2006.01)

(52) U.S. Cl.
 CPC ......... *G01N 21/31* (2013.01); *G01N 33/0027* (2013.01)

(58) Field of Classification Search
 CPC ........... G01N 21/31; G01N 2021/3196; G01N 2021/399; G01N 2201/1211; G01N 2201/1218; G01N 21/39
 See application file for complete search history.

(56) References Cited

U.S. PATENT DOCUMENTS

| | | |
|---|---|---|
| 5,332,901 A | 7/1994 | Eckles et al. |
| 5,900,635 A | 5/1999 | Weckstrom |
| (Continued) | | |

FOREIGN PATENT DOCUMENTS

| | | |
|---|---|---|
| EP | 3995813 A | 5/2022 |
| JP | 2010-512536 A | 4/2010 |
| (Continued) | | |

OTHER PUBLICATIONS

EESR dated May 28, 2024 issued in EP patent application No. 21811914.7.

(Continued)

*Primary Examiner* — Tarifur R Chowdhury
*Assistant Examiner* — Roberto Fabian, Jr.
(74) *Attorney, Agent, or Firm* — Brooks Kushman P.C.

(57) ABSTRACT

The invention is for measuring the concentration of a target component accurately, and is an analysis device that analyzes a target component included in a sample. The analysis device includes a light source that outputs the reference light toward the sample, a photodetector that detects an intensity of sample light that is the reference light having transmitted through the sample, a parameter determining unit that determines a parameter representing a change in a light absorption spectrum of the target component or a change in a light absorption spectrum of an interference component, the change being caused by a coexisting component included in the sample or by a wavelength shift of the reference light, and a concentration calculating unit that calculates a corrected concentration of the target component, by using the parameter representing the change in the light absorption spectrum.

13 Claims, 10 Drawing Sheets

(56) References Cited

U.S. PATENT DOCUMENTS

| | | | |
|---|---|---|---|
| 6,147,351 A | 11/2000 | Huiku | |
| 9,857,267 B1 | 1/2018 | Nelson, Jr. et al. | |
| 2003/0160173 A1* | 8/2003 | Ershov | G01N 21/39 250/338.5 |
| 2009/0006004 A1* | 1/2009 | Sens | G01J 3/4406 702/23 |
| 2013/0250301 A1* | 9/2013 | Feitisch | G01J 3/0297 356/409 |
| 2016/0132617 A1 | 5/2016 | Liu et al. | |
| 2017/0059477 A1 | 3/2017 | Feitisch et al. | |

FOREIGN PATENT DOCUMENTS

| | | | |
|---|---|---|---|
| JP | 2011-209242 A | | 10/2011 |
| JP | 2014102152 A | * | 6/2014 |
| JP | 2016-090521 A | | 5/2016 |
| JP | 2018-096974 A | | 6/2018 |
| JP | 2019-020230 A | | 2/2019 |
| JP | 2020-106528 A | | 7/2020 |
| WO | WO2008/072167 A | | 6/2008 |
| WO | WO2014/112502 A | | 7/2014 |
| WO | WO2021/005900 A | | 1/2021 |

OTHER PUBLICATIONS

International Search Report dated Aug. 17, 2021 issued for International application No. PCT/JP2021/019833.

* cited by examiner

ANALYSIS DEVICE, PROGRAM FOR ANALYSIS DEVICE, AND ANALYSIS METHOD

CROSS-REFERENCE TO RELATED APPLICATIONS

This application is the U.S. national phase of PCT Application No. PCT/JP2021/019833, filed May 25, 2021, which claims priority to Japanese Patent Application No. 2020-094709, filed May 29, 2020, the disclosures of which are incorporated in their entirety by reference herein.

TECHNICAL FIELD

The present invention relates to an analysis device and the like used in applications such as gas component analysis.

BACKGROUND ART

Conventionally, as disclosed in Patent Literature 1, there has been an analysis method for quantifying the concentration of a gas to be measured, by modulating an injection current of a semiconductor laser and sweeping its oscillation wavelength, and obtaining an absorption spectrum of the measurement-target gas (tunable diode laser absorption spectroscopy (TDLAS)).

CITATION LIST

Patent Literature

Patent Literature 1: JP 2016-90521 A

SUMMARY OF INVENTION

Technical Problem

However, in the absorption spectroscopy that uses a laser, such as the TDLAS, the form of the absorption spectrum may change not only because of the effect of an interference component having a light absorption spectrum overlapping with that of the target component (interference effect), but also because of a change in the concentration of a coexisting component coexisting at a high concentration (about several % to several lens %) (coexistent effect). Specifically, the width of the light absorption spectrum broadens, and the absorption peak drops (broadening). As a result, a concentration measurement of the target component may suffer from an error. When the concentration of the target component itself is high, the target component itself becomes a coexisting component, and the coexistent effect occurs due to a concentration change in the target component itself (self-broadening). In other words, a coexisting component can be said to be a component that gives a broadening effect to the component itself or to another component. In addition, in the absorption spectroscopy that uses a laser, such as the TDLAS, the concentration of the target component also suffers from a measurement error due to a wavelength shift in the light emitted from the laser, the wavelength shift being caused by a change in factors such as the ambient temperature. In other words, in any one of these cases, the light absorption spectrum of the target component may change, and the resultant concentration measurement of the target component may suffer from an error.

The present invention has been made in consideration of the problem described above, and a main object of the present invention is, in an analysis device that uses light absorption, to correct a change in a light absorption spectrum caused by a coexistent effect of a coexisting component or by a wavelength shift, and to make an accurate measurement of the concentration of the target component.

As illustrated in FIG. 10(A), it has been known that, a light absorption spectrum broadened due to the effect of a coexisting component has a wider spectrum and a lower absorption peak depending on the concentration of the coexisting component, but the total area of the light absorption spectrum remains almost unchanged. When there is a pressure fluctuation, by contrast, although the light absorption spectrum broadens, the height of the absorption peak remains almost unchanged, as illustrated in FIG. 10(B).

Therefore, focusing on the difference and the similarity between a change resulting from a coexistent effect and that resulting from the pressure fluctuation, in the light absorption spectrum, the inventors of the present application newly introduced a broadening factor $F_B$, which represents a rate of a change in the light absorption spectrum of the target component, caused by the coexisting component included in a sample. The inventors then have found out that, denoting an absorbance signal under a certain pressure P as A (t, P), an absorbance signal A' (t, P) resultant of broadening by the broadening factor $F_B$, which is caused by the coexistent effect, can be approximated using the following equation.

$$A'(t, P) \approx \frac{A(t, PF_B)}{F_B} \qquad \text{[Equation 1]}$$

In other words, a change in the spectrum caused by a coexistent effect is almost the same as that resulting from changes in the pressure multiplied by a factor of $F_B$ and in the absorbance multiplied by a factor of $1/F_B$. The basic concept of the present invention is to use this relation to convert the broadening resultant of a coexistent effect into a change in the pressure, and to make a correction for the coexistent effect simultaneously with that for pressure.

In addition, because the light absorption spectrum also changes due to a wavelength shift in the light source caused by a change in the ambient temperature or the like, it is also necessary to detect and to correct this change.

Solution to Problem

In other words, an analysis device according to the present invention is an analysis device that analyzes a target component included in a sample, the analysis device including: a light source that irradiates the sample with reference light; a photodetector that detects an intensity of sample light that is the reference light having transmitted through the sample; a parameter determining unit that determines a parameter representing a change in a light absorption spectrum of the target component or a change in a light absorption spectrum of an interference component, the change being caused by a coexisting component included in the sample or by a wavelength shift of the reference light; and a concentration calculating unit that calculates a corrected concentration of the target component, from an intensity-related signal related to the intensity of the sample light, by using the parameter representing the change in the light absorption spectrum.

Because such a configuration calculates a corrected concentration of the target component, being corrected using a parameter representing a change in the light absorption spectrum of the target component or of the interference component, the change resulting from a coexisting component included in the sample or a wavelength shift of the reference light, it is possible to correct a change in the light absorption spectrum caused by the coexistent effect of a coexisting component or that caused by a wavelength shift, and to measure the concentration of the target component highly accurately.

Examples of the parameter representing the change in the light absorption spectrum include a broadening factor and a wavelength shift amount of the reference light, the broadening factor representing a rate of the change in the light absorption spectrum of the target component or the change in the light absorption spectrum of the interference component, the change being caused by tire coexisting component included in the sample.

With this, the concentration calculating unit calculates a corrected concentration of the target component, by correcting the coexistent effect of the coexisting component or the wavelength shift of the reference light, using the intensity-related signal related to the intensity of the sample light, and the broadening factor or the wavelength shift amount described above.

The parameter determining unit may determine the broadening factor by fitting reference data to sample data, the reference data being data related to light absorption signals of the target component and of the interference component the broadening factor of which or a pressure of which is known, and the sample data being data related to a light absorption signal obtained from the intensity of the sample light. The fitting herein means comparing and matching the sample data with the reference data. Note that, before using in the comparison and the matching, the reference data is converted using the pressure value of the sample and the relationship of the equation mentioned above (Equation 1). An example of a specific method of the comparison and matching include a non-linear least squares method involving an iterative calculation using the steepest descent, the Gauss-Newton method, or the Levenberg-Marquardt algorithm, for example, The parameter determining unit may also determine the broadening factor by using relationship data indicating a relationship between concentrations of the coexisting component and the broadening factor, and a measured concentration of the coexisting component.

The parameter determining unit may determine a wavelength shift amount by fitting reference data to sample data, the reference data being data related to light absorption signals of the target component and of the interference component for which a wavelength shift amount is known, and the sample data being data related to a light absorption signal obtained from the intensity of the sample light.

The parameter determining unit may also determine the wavelength shift amount of the reference light by using relationship data indicating a relationship between ambient temperatures and wavelength shift amounts, and a measured ambient temperature.

Preferably, the analysis device further includes a correlation value calculating unit that calculates a correlation value between the intensity-related signal related to the intensity of the sample light and a predetermined feature signal. The concentration calculating unit calculates a corrected concentration of the target component, the corrected concentration being corrected for the coexistent effect of the coexisting component or for the wavelength shift of the reference light, using the correlation value and the parameter representing the change in the light absorption spectrum of the target component or the change in the light absorption spectrum of the interference component.

With this configuration, the correlation value between the intensity-related signal related to the intensity of the sample light and the feature signal is calculated, and the concentration of the target component is calculated using the calculated correlation value. Therefore, it is possible to get a grasp of the feature of the absorption signal using a much smaller number of variables, without convening the absorption signal into the absorption spectrum, and is also possible to measure the concentration of the target component by a simple calculation, without performing a complicated spectrum calculation process. For example, general spectral fitting requires several-hundred data points, but in the present invention, the concentration can be calculated at an accuracy equivalent thereto by using several to several tens of correlation values at most. As a result, a processing load can be reduced dramatically, and a high-performance processing unit will be no longer necessary. Furthermore, the cost and the size of the analysis device can be reduced.

Preferably, the analysis device according to the present invention is an analysis device unit analyzes a target component in a sample including one or more interference components interference effects of which are to be removed, wherein the correlation value calculating unit calculates a plurality of correlation values using a number of feature signals equal to or more than a sum of a number of types of the target component and a number of types of the interference component, and the concentration calculating unit calculates the concentration of the target component using the plurality of correlation values and the parameter representing the change in the light absorption spectrum of the target component or the change in the light absorption spectrum of each one of the one or more interference components.

Preferably, the analysis device according to the present invention further includes a storage unit that stores a sole correlation value that is a correlation value between a per unit concentration of the target component and a per unit concentration of each of the plurality of interference components, the sole correlation value being obtained from the intensity-related signal when only the corresponding interference component exists with the target component, and from the plurality of feature signals, wherein the concentration calculating unit calculates the concentration of the target component using a plurality of correlation values obtained by the correlation value calculating unit, the plurality of sole correlation values, and the parameter representing the change in the light absorption spectrum of the target component or the changes in the interference components.

Specifically, it is preferable for the concentration calculating unit to correct the plurality of sole correlation values by using the parameter representing the change in the light absorption spectrum of the target component or the change in the light absorption spectrum of the interference component, and to calculate the concentration of the target component by using the plurality of corrected sole correlation values and the plurality of correlation values obtained by the correlation value calculating unit.

With this configuration, it is possible to determine the concentration of the target component by removing the interference effect and the coexistent effect of the coexisting component or the effect of the wavelength shift of the reference light, using a simple and reliable operation of solving simultaneous equations including several to several tens of elements at most.

More specifically, it is preferable that the concentration calculating unit calculates the concentration of the target component by solving simultaneous equations including the plurality of correlation values obtained by the correlation value calculating unit, the plurality of corrected sole correlation values, and the concentrations of the target component and each of the interference components.

For the purpose of correcting the sole correlation values, it is preferable to obtain the sole correlation values corresponding to each of the components under a plurality of known pressures or with a plurality of known wavelength shifts of the reference light, and to store the sole correlation values in advance in the storage unit. In this manner, a sole correlation value can be corrected using the broadening factor or the wavelength shift amount determined by the parameter determining unit. Note that the sole correlation values stored in advance in the storage unit may be obtained with known broadening factors, instead of known pressures, but it is not easy to create a condition where a broadening factor is known. Therefore, it is preferable to use sole correlation values obtained under known pressures.

In addition, preferably, when there is a fluctuation in the sample pressure during a measurement, the sample pressure is monitored using a pressure sensor or the like, and the sole correlation value is corrected using the pressure value. In this manner, it becomes possible to correct the coexistent effect of the coexisting component and the effect of the pressure fluctuation at the same lime.

At this time, the concentration calculating unit may correct the sole correlation value using the sole correlation values of each of the components, the sole correlation values being obtained for each of a plurality of known pressures of the sample, the plurality of correlation values obtained by the correlation value calculating unit, the pressure value inside the cell, and a relationship represented by following equation (Equation 2).

$$s'_{ij} = \frac{s_{ij}(F_B \cdot p)}{F_B} \quad \text{[Equation 2]}$$

Where p denotes the pressure of the sample measured by the pressure sensor, $F_B$ denotes the broadening factor determined by the broadening factor determining unit, $s_{ij}$ denotes a sole correlation value corresponding to each of the pressures stored in the storage unit, and $s'_{ij}$ denotes a corrected sole correlation value. The above equation (Equation 2) indicates that the corrected sole correlation value $s'_{ij}$ is obtained by, for a sole correlation value $s_{ij}(p)$ with a sample pressure p at time of a sample measurement, by multiplying $1/F_B$ to the sole correlation value resultant of multiplying the pressure by $F_B$.

When the interference component is also affected by the broadening caused by the coexisting component, it is also possible to determine a separate broadening factor for the interference component, and to correct the sole correlation value of the interference component. In this manner, the measurement accuracy can be further improved.

A program for an analysis device according to the present invention is a program applied to an analysis device including a light source that irradiates a sample with reference light, and a photodetector that detects sample light having transmitted through the sample, the program causing the analysis device to implement functions as: a parameter determining unit that determines a parameter representing a change in a light absorption spectrum of a target component or a change in a light absorption spectrum of an interference component, the change being caused by a coexisting component included in the sample or by a wavelength shift of the reference light; and a concentration calculating unit that calculates a corrected concentration of the target component, from an intensity-related signal related to an intensity of the sample light, by using the parameter representing the change in the light absorption spectrum.

Furthermore, an analysis method according to the present invention is an analysis method for analyzing a target component included in a sample by using a light source that irradiates the sample with reference light, and a photodetector that detects sample light having transmitted through the sample, the analysis method including: determining a parameter representing a change in a light absorption spectrum of the target component or a change in a light absorption spectrum of an interference component, the change being caused by a coexisting component included in the sample or by a wavelength shift of the reference light; and calculating a corrected concentration of the target component, from an intensity-related signal related to an intensity of the sample light, by using the parameter representing the change in the light absorption spectrum.

Advantageous Effects of Invention

According to the present invention described above, it is possible to measure the concentration of a target component accurately, in an analysis device that uses a light absorption, by applying a correction for a change in the light absorption spectrum caused by the coexistent effect of a coexisting component or a wavelength shift in die reference light.

REFERENCE SIGNS LIST

Figure 1:
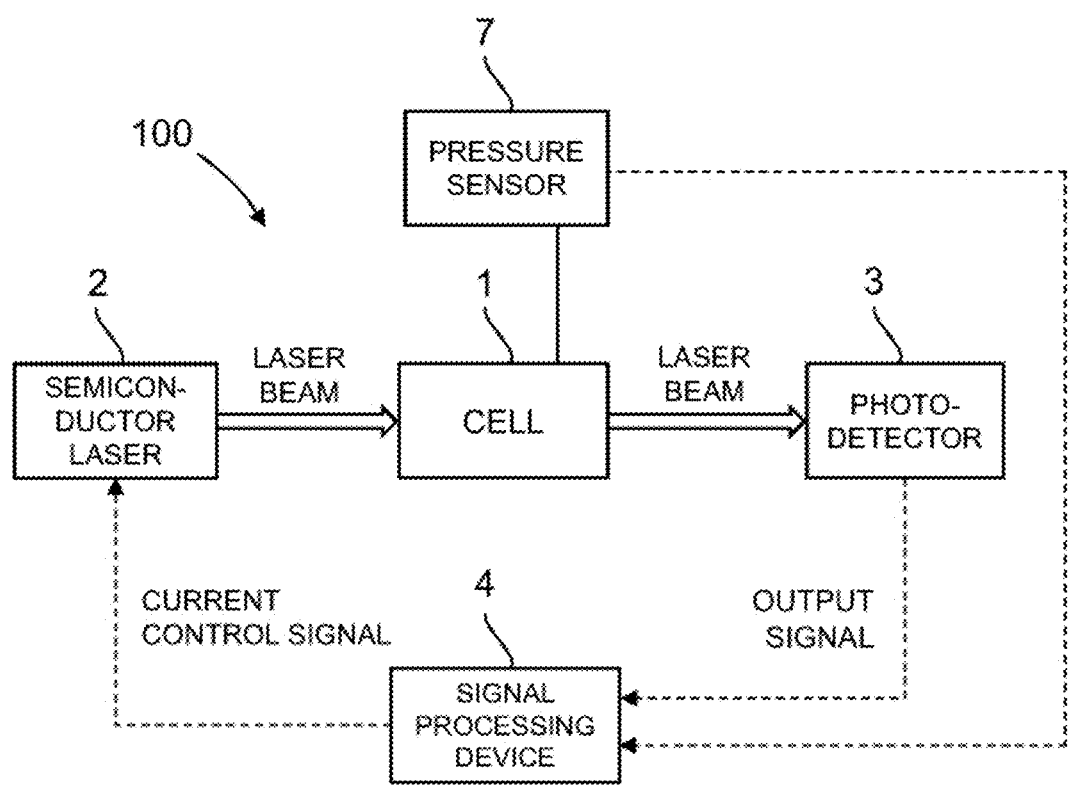
FIG. 1 is an overall schematic of an analysis device according to a first embodiment of the present invention.

100 analysis device
1 cell 2 light source (semiconductor laser)
3 photodetector
4 signal processing device
61 logarithmic operation unit
62 correlation value calculating unit
63 storage unit
64 broadening factor determining unit
65 concentration calculating unit
66 wavelength shift determining unit
7 pressure sensor

DESCRIPTION OF EMBODIMENTS

First Embodiment (Coexistent Effect Correcting Function)

An analysis device 100 according to the present embodiment is a concentration measurement device that measures the concentration of a target component (such as CO or $CO_2$, in this example) included in sample gas such as exhaust gas, and includes, as illustrated in FIG. 1. a cell 1 into which sample gas is introduced, a semiconductor laser 2 that is a light source that irradiates the cell 1 with laser light to be modulated, a photodetector 3 that is provided on the light path of sample light that is laser light passed through the cell 1 and that receives the sample light, a signal processing device 4 that receives an output signal from the photodetector 3 and that calculates the concentration of the target component based on the output signal, and a pressure sensor 7 that monitors the pressure inside the cell 1.

To the analysis device 100 according to the embodiment, an entry channel for introducing the sampling gas into the analysis device 100 is connected, and an exit channel for discharging the gas analyzed by the analysis device 100 is connected. A pump for introducing the sampling gas into the analysis device 100 is provided to the entry channel or the exit channel. The entry channel may also be configured to sample the exhaust gas directly from an exhaust pipe or the like, configured to receive the exhaust gas from a bag in which the exhaust gas is collected, or configured to receive the exhaust gas diluted by a dilution device such as constant volume sampler (CVS), for example.

Each of the units will now be explained.

The cell 1 is made of a transparent material, such as quartz, calcium fluoride, or barium fluoride, that absorbs almost no light within an absorption wavelength range of the target component, and has a light inlet port and an outlet port. Although not illustrated, the cell 1 is provided with an inlet port via which gas is introduced and an outlet port via which the internal gas is discharged, and the sample gas is introduced into the cell 1 via the inlet port, and sealed inside the cell 1.

In this example, the semiconductor laser 2 is a quantum cascade laser (QCL), which is a type of the semiconductor laser 2, and oscillates a mid-infrared laser beam (4 to 12 µm). The semiconductor laser 2 can modulate (change) the oscillation wavelength using a given current (or voltage). As long as the oscillation wavelength is can be changed, another type of laser may be used. It is also possible to change the oscillation wavelength by changing the temperature or the like.

In this example, a relatively inexpensive thermal photodetector, such as a thermopile, is used as the photodetector 3, but another type of photodetector such as a quantum type photoelectric element having good responsiveness such as HgCdTe, InGaAs, InAsSb, or PbSe may also be used.

Figure 2:
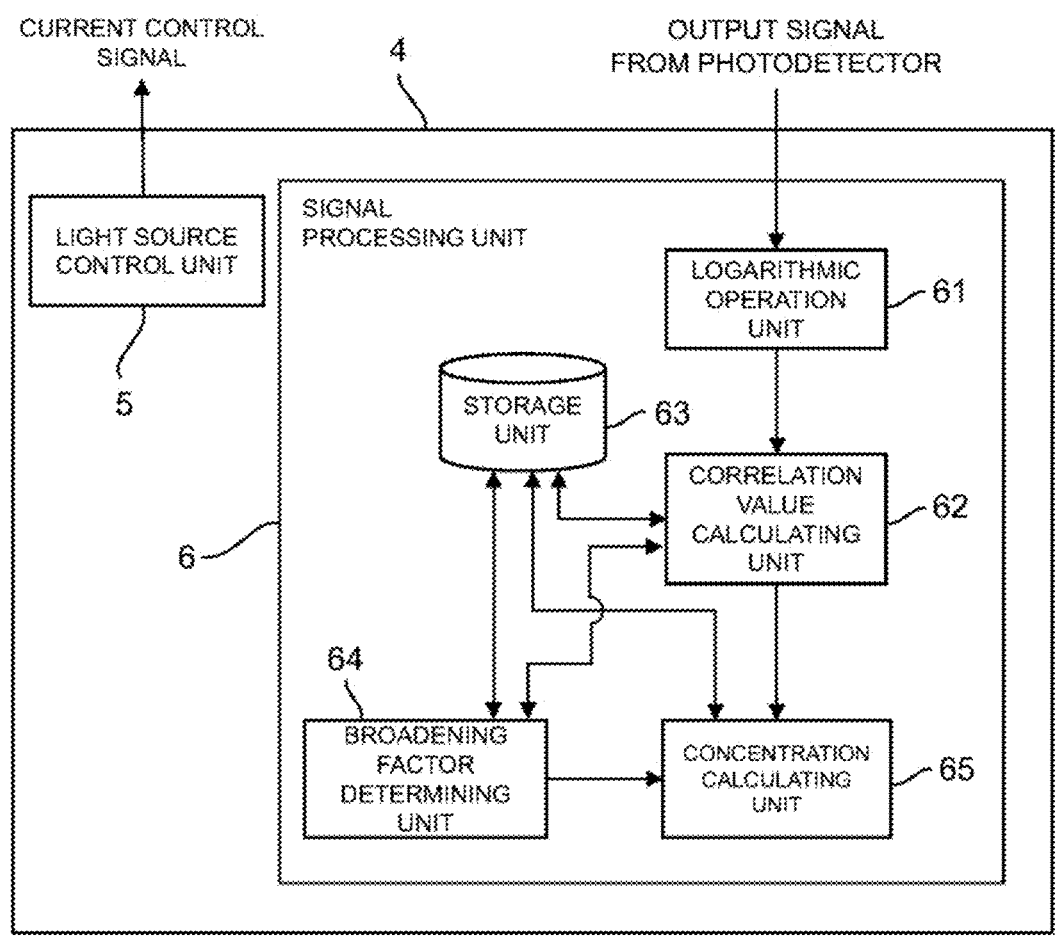
FIG. 2 is a functional block diagram of a signal processing device according to the embodiment.

The signal processing device 4 includes an analog electric circuit including a buffer, an amplifier, and the like, a digital electric circuit including a CPU, a memory, and the like, and an AD converter, a DA converter, and the like that serve as mediators between the analog/digital electric circuits. The signal processing device 4 functions as a light source control unit 5 for controlling the output of the semiconductor laser 2, and as a signal processing unit 6 that receives an output signal of the photodetector 3 and performs an arithmetic operation of the signal to calculate the concentration of the target component, by causing the CPU and peripheral devices to cooperate with each other in accordance with a predetermined computer program stored in a predetermined area of the memory, as illustrated in FIG. 2.

The pressure sensor 7 monitors the pressure of the sample. In this example, the pressure sensor 7 measures the absolute pressure inside the cell 1, and, a silicon-piezoresistive absolute pressure sensor is used in this example. Before a measurement is to be carried out, the pressure inside the cell is adjusted to approximately 20 to 30 kPa using a pump and a pressure regulator, not illustrated.

Each of the units will now be explained in detail.

The light source control unit 5 outputs a current (or voltage) control signal to control a current source (or a voltage source) of the semiconductor laser 2. Specifically, the light source control unit 5 changes a driving current (or a driving voltage) for the semiconductor laser 2 at a predetermined frequency, and modulates the oscillation wavelength of the laser light output from the semiconductor laser 2 at a predetermined frequency, with respect to a center wavelength. As a result, the semiconductor laser 2 emits modulated light having been modulated at the predetermined modulation frequency.

Figure 3:
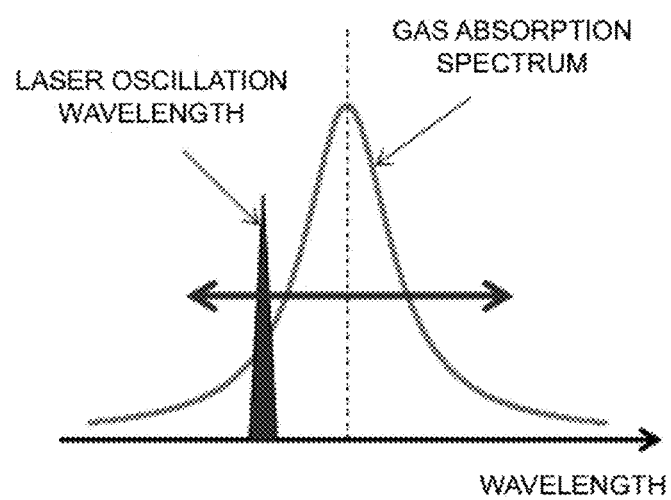
FIG. 3 is a schematic diagram illustrating a method of modulating a laser oscillation wavelength in the embodiment.
Figure 4:
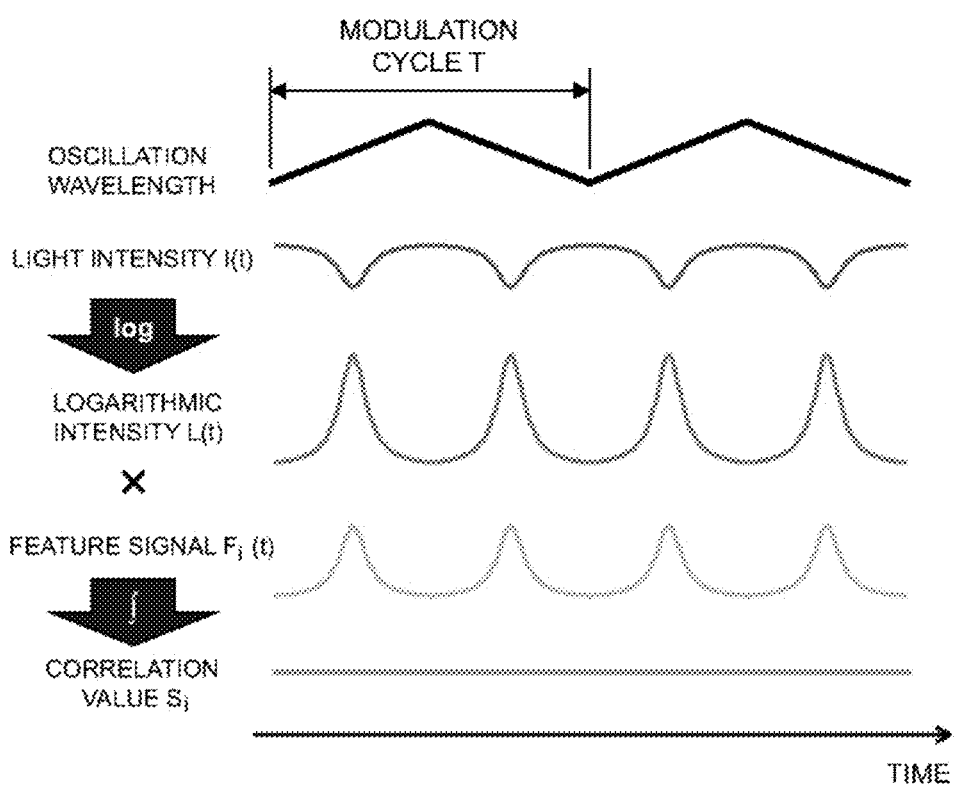
FIG. 4 is a time-series graph illustrating an example of an oscillation wavelength, a light intensity I(t), a logarithmic intensity L(t), a feature signal $F_i$(t). and a correlation value $s_i$(t) according to the embodiment.

In this embodiment, the light source control unit 5 changes the driving current to a triangular wave, and modulates the oscillation frequency to a triangular wave (see "oscillation wavelength" in FIG. 4). In practice, the driving current is modulated by another function so that the oscillation frequency delineates a triangular waveform. As illustrated in FIG. 3, the oscillation wavelength of the laser light is configured to be modulated using the peak of the light absorption spectrum of the target component as the center wavelength. The light source control unit 5 may also change the driving current to a sinusoidal form, a saw teeth form, or an arbitrary functional form to modulate the oscillation frequency to a sinusoidal form, a saw-teeth form, or an arbitrary functional form.

The signal processing unit 6 includes a logarithmic operation unit 61, a correlation value calculating unit 62, a storage unit 63, a broadening factor determining unit 64 that is a parameter determining unit, and a concentration calculating unit 65.

The logarithmic operation unit 61 executes a logarithmic operation to the light intensity signal that is an output signal of the photodetector 3. The function I(t) that represents a change in the light intensity signal obtained over time with the photodetector 3 will be indicated as "light intensity I(t)" in FIG. 4. and the change in the light intensity applied with the logarithmic operation will be as indicated as "logarithmic intensity L(t)" in FIG. 4.

The correlation value calculating unit 62 calculates a correlation value between an intensity-related signal that is related to an intensity of the sample light, and each of a plurality of predetermined feature signals. A feature signal is a signal by which a waveform feature of the intensity-related signal is extracted, by being correlated with the intensity-related signal. As the feature signal, it is possible to use a sine wave signal, or other various types of signals corresponding to respective waveform features to be extracted from the intensity-related signal.

An example in which the feature signal other than a sine wave signal is used will now be explained. The correlation value calculating unit 62 calculates a correlation value between an intensity-related signal that is related to the intensity of the sample light and each of a plurality of feature signals from which different correlation values with the intensity-related signal can lie found, being different from that found with a sine wave signal (sine function). As the intensity-related signal, the correlation value calculating unit 62 uses a light intensity signal applied with a logarithmic operation (logarithmic intensity L(t)).

The correlation value calculating unit 62 also calculates, using the equation below (Equation 3), a plurality of sample correlation values $S_i$ that are correlation values between the intensity-related signal of the sample light and the feature signals $F_i(t)$ (i=1, 2, ..., n), the number of which is equal to or greater than the sum of the number of the types of target components and the number of types of interference components from which the interference effects are to be removed. Note that T in the following equation (Equation 3) denotes a modulation cycle.

$$S_i = \int_{-t/2}^{T/2} L(t) \cdot F_i(t) dt (i=1,2, \ldots, n)$$

$$R_i = \int_{-T/2}^{T/2} L_0(t) \cdot F_s(t) dt (i=1,2, \ldots, n) \quad \text{[Equation 3]}$$

When the samples correlation values are to be calculated, the correlation value calculating unit 62 preferably calculates corrected sample correlation values $S'_i$ by subtracting reference correlation values $R_i$ that are the correlation values between the intensity-related signal $L_0(t)$ of the reference light and the respective feature signals $F_i(t)$, from the correlation values $S_i$ between the intensity-related signal L(t) of the sample light and the respective feature signals $F_i(t)$, as indicated in Equation (3). In this manner, it is possible to achieve correlation values that are proportional to the concentrations of the target component and of the interference component, with the offsets included in the sample correlation value removed. Therefore, the measurement error can be reduced. Note that a configuration not subtracting the reference correlation values is also possible.

The timing at which the reference light is obtained may be simultaneously with when the sample light is obtained, or timing before or after the measurement, or may be any timing. It is also possible to obtain and to store the intensity-related signal of the reference light or the reference correlation value in the storage unit 63 in advance. A possible method for obtaining the reference light simultaneously includes, for example, is providing two photodetectors 3, splitting the modulated light from the semiconductor laser 2 with a beam splitter or the like, and using one tor the measurement of the sample light and the other for the measurement of the reference light.

In the present embodiment, the correlation value calculating unit 62 uses a function better capable of capturing a waveform feature of a logarithmic intensity L(t) as a feature signal $F_i(t)$, than with a sine function. When it is desirable to also correct the coexistent effect of the coexisting component on the target component, in a sample gas containing the target component and one interference component, three feature signals $F_1(t)$, $F_2(t)$, and $F_3(t)$ may be used. As the three feature signals, for example, it is possible to use a function based on a Lorentz function that is close to the form of the absorption spectrum, as indicated as the following equation (Equation 4), and a partial differential function related to a Lorentz width of a function that is based on the Lorentz function. w in the equation (Equation 4) denotes the Lorentz width, and s denotes a shift in the absorption peak with respect to the position thereof at the reference time, the shift being resultant of a wavelength shift. A denotes an arbitrary constant, and $A_1$, $A_2$, and $A_3$ are offsets for adjusting $F_1(t)$, $F_2(t)$, and $F_3(t)$ to zero, respectively, when $F_1(t)$, $F_2(t)$, and $F_3(t)$ are integrated over the modulation cycle. When such functions are used as the feature signals, a spectral change caused by the coexistent effect can he captured at a higher sensitivity, and the coexistent effect can be corrected more accurately. As a feature signal, a function based on the Voigt function or a function based on the Gaussian function, for example, may also be used, instead of the function based on the Lorentz function. By using such a function for the feature signals, higher correlation values can be obtained than those with a sine function, so that measurement accuracy can be improved.

$$F_1(t) = \frac{A}{1 + \left(\frac{|t| - s_1}{w_1}\right)^2} - A_1 \quad \left(-\frac{T}{2} \leq t \leq \frac{T}{2}\right) \quad \text{[Equation 4]}$$

$$F_2(t) = \frac{A}{1 + \left(\frac{|t| - s_2}{w_1}\right)^2} - A_2 \quad \left(-\frac{T}{2} \leq t \leq \frac{T}{2}\right)$$

$$F_3(t) = \frac{\partial F_j}{\partial w_1} - A_3 \quad \left(-\frac{T}{2} \leq t \leq \frac{T}{2}\right)$$

At this lime, it is preferable to adjust the offset of a feature signal in such a manner that the DC component is removed, that is, so that the offset becomes zero as a result of integrating the feature signal over the modulation cycle. In this manner, it is possible to remove the effect of an offset added to the intensity-related signal due to a fluctuation of the light intensity. It is also possible to, instead of removing the DC component of the feature signal, remove the DC component of tire intensity-relaxed signal, or to remove the DC component of both of the feature signal and the intensity-related signal. Furthermore, actual measurements of the absorption signal of the target component and/or the interference component, or simulations thereof may also be used as the feature signals.

Note that by setting the three feature signals $F_1(t)$, $F_2(t)$, and $F_3(t)$ to orthogonal functions that are orthogonal to one another, or to functions close to orthogonal functions, the features of the logarithmic intensities L(t) can be extracted more efficiently, and the accuracies of the concentrations obtained by simultaneous equations, which will be described later, can be improved.

The storage unit 63 stores therein a sole correlation value that is a correlation value between per unit concentrations of the target component and of each of the interference components under a known pressure inside the cell, the sole correlation value being obtained from the intensity-related signal when only the corresponding component exists with the target component, and from the feature signal $F_i(t)$. The feature signal $F_i(t)$ used in obtaining the sole correlation value is the same as the feature signal $F_i(t)$ used in the correlation value calculating unit 62. In this manner, sole correlation values corresponding to various respective pressures inside the cell are stored in the storage unit 63.

When the sole correlation values are stored, the storage unit 63 preferably stores therein the sole correlation values resultant of subtracting the reference correlation values from the respective correlation values of the time when there is only one of the interference components with the target component, and of applying a correction for converting the sole correlation values into correlation values per unit concentration. The resultant correlation values are correlation values with the offsets included in the sole correlation values removed, and being proportional to the concentrations of the target component and of the interference component. Therefore, it is possible to reduce the measurement errors. Note that a configuration not subtracting the reference correlation values is also possible.

The broadening factor 64 determines a broadening factor $F_B$ representing a rate of the change in the light absorption spectrums of a target component and an interference component, the changes being caused by a coexisting component included in the sample. When the coexistent effect of the coexisting component on the interference component should also be taken into consideration, another broadening factor $F_B$ is added, and determined for that component.

As a method of determining the broadening factor $F_B$, for example, the following sequence (a) or (b) is possible.

(a) The broadening factor Fa is determined by obtaining sole correlation values $s_{itar}(p_k)$ and $s_{iint}(p_k)$ corresponding to the target component and of the interference component, respectively, with the feature signal $F_i(t)$, using each of the pressures $p_k$ (k=1, 2, . . . , 1) in the cell, in advance, and by comparing and matching the sample correlation value collected at the time of measurement with these sole correlation values. Note that, before the sole correlation values are used in the comparison and matching, the sole correlation values are convened using the pressure value of the inside of the cell and the relationship expressed in the equation described above (Equation 2). With this method, the required number of feature signals is equal to or more than the sum of the number of types of target component, the number of types of interference component, and the number of types of broadening factors.

(b) The broadening factor $F_B$ is determined using the relationship data indicating the relationship between concentrations of the coexisting component and broadening factors $F_B$, with the measured concentration of the coexisting component.

At this time, the relationship data is generated in advance by obtaining a broadening factor $F_B$ for each concentration of the coexisting component through an experiment or a calculation. The measured concentration of the coexisting component may be collected using the analysis device 100 according to the present embodiment before correcting the coexistent effect, or the concentration of the coexisting component may be collected using another analysis device.

The concentration calculating unit 65 calculates the concentration of the target component using a sample correlation value obtained by the correlation value calculating unit 62.

Specifically, the concentration calculating unit 65 calculates a concentration of the target component based on the sample correlation values obtained by the correlation value calculating unit 62. the broadening factor $F_B$ determined by the broadening factor determining unit 64, and the sole correlation values stored in the storage unit 63. More specifically, the concentration calculating unit 65 corrects the sole correlation values stored in the storage unit 63 to obtain the corrected sole correlation values based on the broadening factor $F_B$ obtained by the broadening factor determining unit 64. The concentration calculating unit 65 then calculates the concentration of the target component by solving a simultaneous equation including the sample correlation values obtained by the correlation value calculating unit 62, the corrected sole correlation values corresponding to the determined broadening factors $F_B$, and the concentrations of the target component and of the interference components.

An example of an operation of the analysis device 100 will now lie explained, also as a detailed description of each of the units. Hereinafter, it is assumed that sample gas contains one target component and one interference component.

< Reference Measurement>

To begin with, the light source control unit 5 controls the semiconductor laser 2 to modulate the wavelength of the laser light using a predetermined modulation frequency and modulation depth, around the peak of the absorption spectrum of the target component. Before carrying out the reference measurement using a span gas, the reference measurement using a zero gas may be performed to measure the reference correlation values.

A span gas (gas the component concentrations of which are known) is introduced into the cell 1 by an operator or automatically, and reference measurement is carried out. The reference measurements are collected using a span gas only containing the target component, and a span gas only containing the interference component.

Specifically, in the reference measurement, the logarithmic operation unit 61 receives output signals from the photodetector 3, under pressure in the respective cells, and calculates their logarithmic intensities L(t). The correlation value calculating unit 62 then calculates a correlation value between each of the logarithmic intensities L(t) and each of the three feature signals $F_1(t)$, $F_2(t)$, and $F_3(t)$. The correlation value calculating unit 62 then subtracts the reference correlation values from the respective correlation values, and divides each of the result by the corresponding span gas concentration to calculate a sole correlation value that is a correlation values per unit concentration of the corresponding span gas. Instead of calculating the sole correlation value per unit concentration, the span gas concentration and the sole correlation value of the span gas may be stored.

Specifically, this is done in the manner described below. By adjusting the pressure in the cell to $p^*$ and introducing the span gas only containing the target component into the cell I, the correlation value calculating unit 62 calculates the correlation values $S_{1tar}(p_k)$, $S_{2tar}(p_k)$, and $S_{3tar}(p_k)$ for the target component. $S_{1tar}(p_k)$ herein is a correlation value with the first feature signal. $S_{2tar}$ (pk), is a correlation value with the second feature signal, and $S_{3tar}(p_k)$ is a correlation value with the third feature signal. The correlation value calculating unit 62 then calculates the sole correlation values $S_{1tar}(p_k)$, $S_{2tar}(p_k)$, and $S_{3tar}(p_k)$ by dividing the values resultant of subtracting the reference correlation values $R_i$ from the correlation values $S_{1tar}(p_k)$, $S_{2tar}(p_k)$, and $S_{3tar}(p_k)$, respectively, by the span gas concentration $c_{tar}$ of the target component. This procedure is performed at each pressure while sequentially changing the pressure in the cell (every 1 kPa between 20 kPa and 40 kPa, for example) using a method such as adjusting a pressure adjuster for adjusting the pressure in the cell, and relationships between the sole correlation values at that pressure and the pressure are stored. The span gas concentration $c_{tar}$ of the target component is input to the signal processing unit 6 by a user or the like in advance.

The correlation value calculating unit 62 calculates correlation values $S_{1int}(p_k)$, $S_{2inbt}(p_k)$, and $S_{3int}(p_k)$ for the interference component by introducing the span gas only containing the interference component into the cell 1 where the pressure value is adjusted to $p_k$. $S_{1int}(p_k)$ herein is a correlation value with the first feature signal, $S_{2int}(p_k)$ is a correlation value with the second feature signal, and $S_{3int}$ ($p_k$) is a correlation value with the third feature signal. The correlation value calculating unit 62 then calculates the sole correlation values $s_{1int}$ ($p_k$), $s_{2int}$ ($p_k$), and $s_{3int}$ ($p_k$) by dividing the values obtained by subtracting the reference correlation values $R_i$ from the correlation values $S_{1int}$ ($p_k$), $S_{2int}$ ($p_k$), and $S_{3int}$ ($p_k$), respectively, by the span gas concentration $c_{int}$ of the interference component. This procedure is performed at each pressure while sequentially changing the pressure in the cell (for example, every 1 kPa between 20 kPa and 40 kPa), and relationships between the resultant sole correlation values at that pressure and the pressure are stored. The span gas concentration $c_{ont}$ of the interference component is input to the signal processing unit 6 by a user or the like in advance.

The sole correlation values $s_{1tar}$ ($p_k$), $s_{2tar}$ ($p_k$), $s_{3tar}$ ($p_k$), $s_{1int}$ ($p_k$), $s_{2int}$ ($p_k$), and $s_{3int}$ ($p_k$) calculated using the pressures $p_k$ in each of the cells, as described above, are stored in the storage unit 63. The reference measurement may be performed before the shipment of the product, or may be performed regularly.

<Sample Measurements>

The light source control unit 5 controls the semiconductor laser 2 to modulate the wavelength of the laser light using a predetermined modulation frequency and modulation depth, around the peak of the absorption spectrum of the target component.

A sample gas is introduced into the cell 1 by an operator or automatically, and sample measurement is then carried out.

Specifically, in the sample measurement, the logarithmic operation unit 61 receives the output signal from the photodetector 3, and calculates the logarithmic intensity l(t). The correlation value calculating unit 62 then calculates sample correlation values $S_1$, $S_2$, and $S_3$ between the logarithmic intensity L(t) and the feature signals $F_1(t)$, $F_2(t)$, and $F_3(t)$, and calculates sample correlation values $S'_1$, $S'_2$, and $S'_3$ obtained by subtracting the reference correlation values $R_i$ from the calculated sample correlation values, respectively.

In addition, the broadening factor determining unit 64 determines the broadening factor $F_B$ using the method (a) or (b) described above.

Using the sole correlation values at the pressure $p_k$ inside each of the cells, the correlation values stored in the storage unit 63, the pressure value p in the cell measured by the pressure sensor 7. the broadening factor $F_B$ determined by the broadening factor determining unit 64, and the above-described equation (Equation 2), the concentration calculating unit 65 determines the sole correlation values $s'_{1tar}$ and $s'_{2tar}$ of the target component, being corrected with both of the pressure in the cell and the broadening factor, and the sole correlation values $s'_{1int}$ and $s'_{2int}$ of the interference component corrected only with the pressure in the cell (the broadening factor is 1). As a determination method, for example, a method using linear interpolation, or quadratic interpolation, spline interpolation, for example, is possible.

Figure 5:
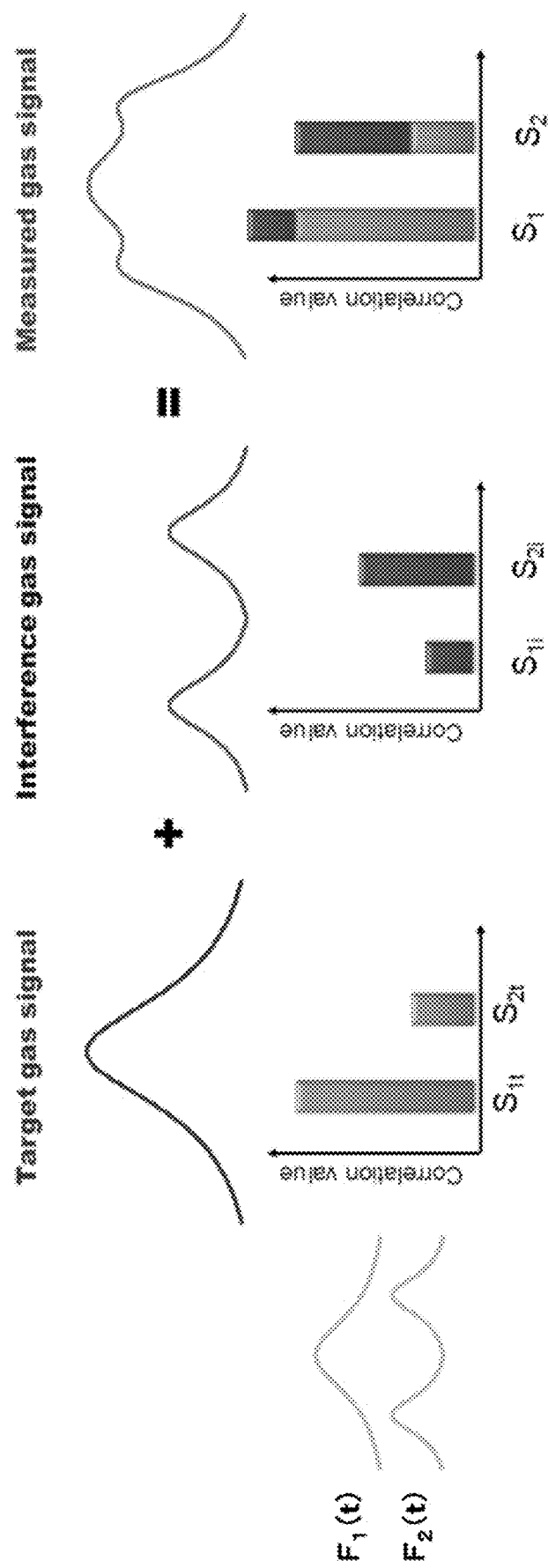
FIG. 5 is a diagram illustrating a conceptual diagram of a concentration calculation using a sole correlation value and an actually measured correlation value according to the embodiment.

The concentration calculating unit 65 then solves the following binary simultaneous equation including the sample correlation values $S'_1$ and $S'_2$ corrected with the reference correlation values calculated by the correlation value calculating unit 62, the corrected sole correlation values $s'_{1tar}$, $s'_{2tar}$, $s'_{1int}$, and $s'_{2int}$, and the concentrations $C_{tar}$ and $C_{int}$ of the target component and the interference component, respectively (see FIG. 5).

$$s'_{1tar} \cdot C_{tar} + s'_{1int} \cdot C_{int} = S'_1$$

$$s'_{2tar} \cdot C_{tar} + s'_{2int} \cdot C_{int} = S'_2 \qquad \text{[Equation 5]}$$

As a result, the concentration $C_{tar}$ of the target component with the interference effect and the coexistent effect removed can be determined by a simple and reliable operation of solving the simultaneous equations indicated as the above equation (Equation 5).

Note that, even if it can be assumed that there are two or more interference components the interference effects of which are to be removed, by adding the sole correlation values corresponding to the number of interference components and solving simultaneous equations having the same number of elements as the number of types of the components, it is possible to similarly determine the concentration of the target component with the interference effect and the coexistent effect removed.

In other words, to generalize, in a case where there are n types of gases in total, including the target component and the interference component, denoting the corrected sole correlation value of the j-th type of the gas with the i-th feature signal as $s'_{ij}$, denoting the concentration of the j-th type of gas as $C_j$, and denoting the sample correlation value in the i-th feature signal $F_i(t)$ as $S_i$, the following equation (Equation 6) is established.

$$\begin{aligned} s'_{11}C_1 + s'_{12}C_2 + s'_{13}C_3 + \ldots + s'_{1n}C_n &= S'_1 \\ s'_{21}C_1 + s'_{22}C_2 + s'_{23}C_3 + \ldots + s'_{2n}C_n &= S'_2 \\ s'_{31}C_1 + s'_{32}C_2 + s'_{33}C_3 + \ldots + s'_{3n}C_n &= S'_3 \\ &\vdots \\ s'_{n1}C_1 + s'_{n2}C_2 + s'_{n3}C_3 + \ldots + s'_{nn}C_n &= S'_n \end{aligned} \qquad \text{[Equation 6]}$$

By solving the simultaneous n-dimensional equation expressed by the equation (Equation 6), it is possible to determine the concentration resultant of correcting the interference effect and the coexistent effect of the target component and the interference component in each gas. Even when the sample contains no interference component, it is possible to determine the concentration resultant of correcting the coexistent effect of the target component and of the coexisting component in each gas, by solving the simultaneous equation with n unknowns.

With the analysis device 100 according to the present embodiment configured in the manner described above, the broadening factor $F_B$ indicating the rate of a change in the light absorption spectrum of the target component, the change caused by the coexisting component, is determined, and the concentration of the target component resultant of correcting the coexistent effect of the coexisting component is calculated using the determined broadening factor $F_B$. Therefore, it is possible to correct the change in the light absorption spectrum of the target component caused by the coexistent effect of the coexisting component, and to measure the concentration of the target component accurately.

In addition, with the analysis device 100 according to the present embodiment, because the correlation value $S_i$ between the logarithmic intensity L(t), which is the intensity-related signal related to the intensity of the sample light, and the plurality of respective feature signals $F_i(t)$ are calculated for the logarithmic intensity L(t). and the concentration of the target component is calculated using the plurality of calculated correlation values $S_i$, it is possible to get a grasp of the features of the absorption signal using a much smaller number of variables, without converting the absorption signal into the absorption spectrum, and also to measure the concentration of the target component with a simple calculation, without performing complicated spectrum calculation processing. For example, general spectral fitting requires several-hundred data points, but in the present invention, the concentration can be calculated at an accuracy equivalent thereto by using several to several tens of correlation values at most. As a result, a load of the processor can be reduced dramatically, and a high-performance processing unit will be no longer necessary. Furthermore, the cost and the size of the analysis device 100 can be reduced.

At this lime, because signals resulting in correlation values that are different from those of a sine wave signal are used as the feature signals, the concentration of the target component can be obtained with an accuracy equivalent to or higher titan that of an analysis device that calculates concentrations using a method using conventional lock-in detection.

Second Embodiment (Wavelength Shift Correction Function)

Figure 6:
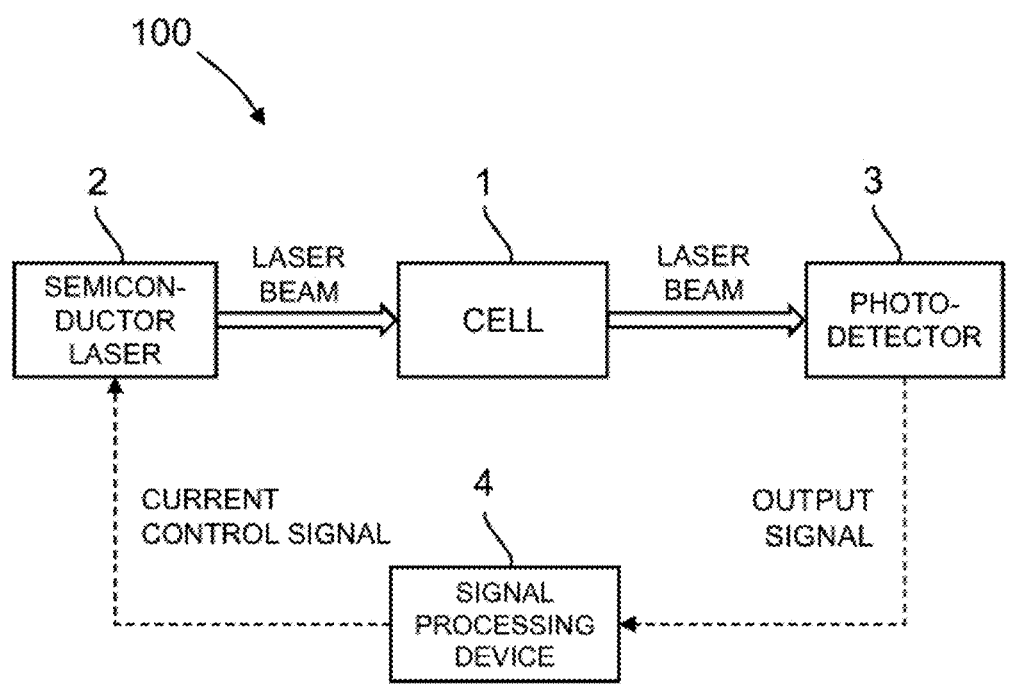
FIG. 6 is an overall schematic view of an analysis device according to a second embodiment of the present invention.

The analysis device 100 according to the present embodiment is a concentration measurement device that measures the concentration of a target component (such as CO or $CO_2$, in this example) included in sample gas such as exhaust gas, and includes, as illustrated in FIG. 6, the cell 1 into which sample gas is introduced, the semiconductor laser 2 that is a light source that irradiates the cell 1 with laser light to be modulated, the photodetector 3 that is provided on the light path of sample light that is laser light passed through the cell 1 and that receives the sample light, and the signal processing device 4 that receives an output signal from the photodetector 3 and that calculates the concentration of the target component based on the output signal. In the second embodiment, functions of elements denoted by the same reference numerals as those in the first embodiment are basically the same as those in the first embodiment, and explanations thereof will be omitted. Differences with respect to the first embodiment will now be explained.

Figure 7:
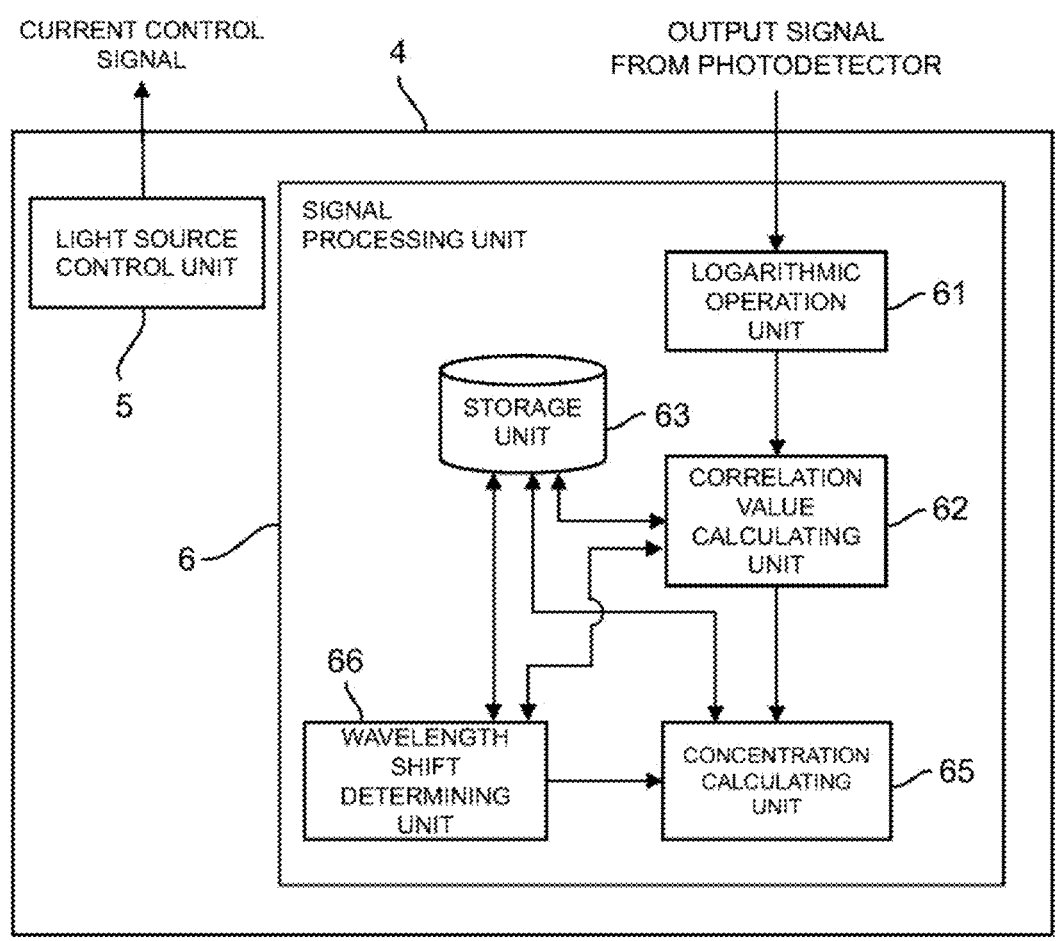
FIG. 7 is a functional block diagram of a signal processing device according to a second embodiment of the present invention.

As illustrated in FIG. 7, the signal processing unit 6 includes lire logarithmic operation unit 61, the correlation value calculating unit 62, the storage unit 63, the concentration calculating unit 65, and a wavelength shift detecting unit 66 that is a parameter determining unit.

In the present embodiment, the correlation value calculating unit 62 uses a function better capable of capturing a waveform feature of a logarithmic intensity L(t) as a feature signal $F_i(t)$, than with a sine function. When it is desirable to also correct the coexistent effect of the wavelength shift in the reference light in a sample gas containing the target component and one interference component, three feature signals $F_1(t)$, $F_2(t)$, and $F_3(t)$ may be used. As the three feature signals, for example, it is possible to use a function based on a Lorentz function that is close to the form of the absorption spectrum, us indicated as the following equation (Equation 7), and a partial differential function related to the shift of a function that is based on the Lorentz function from the position at the reference time, w in the equation (Equation 7) denotes the Lorentz width, and s denotes a shift in the absorption peak with respect to the position thereof at the reference time, the shift being resultant of a wavelength shift. A denotes an arbitrary constant, and $A_1$, $A_2$, and $A_3$ are offsets for adjusting $F_1(t)$, $F_2(t)$, and $F_3(t)$ to zero, respectively, when $F_1(t)$, $F_2(t)$, and $F_3(t)$ are integrated over the modulation cycle. When such functions are used as the feature signals, the spectrum change due to the effect of the wavelength shift of the reference light can be captured with higher sensitivity, and the effect of the wavelength shift of the reference light can be corrected at a higher accuracy. As a feature signal, a function based on the Voigt function or a function based on the Gaussian function, for example, may also be used, instead of the function based on the Lorentz function. By using such a function for the feature signals, higher correlation values can be obtained than diose with a sine function, so that measurement accuracy can be improved.

$$F_1(t) = \frac{A}{1 + \left(\frac{|t| - s_1}{w_1}\right)^2} - A_1 \quad \left(-\frac{T}{2} \le t \le \frac{T}{2}\right) \quad \text{[Equation 7]}$$

$$F_2(t) = \frac{A}{1 + \left(\frac{|t| - s_2}{w_1}\right)^2} - A_2 \quad \left(-\frac{T}{2} \le t \le \frac{T}{2}\right)$$

$$F_3(t) = \frac{\partial F_j}{\partial s_1} - A_3 \quad \left(-\frac{T}{2} \le t \le \frac{T}{2}\right)$$

The storage unit 63 stores therein a sole correlation value that is a correlation value between per unit concentrations of the target component anti of each of the interference components with a known wavelength shift amount of the reference light. The sole correlation value is obtained from the intensity-related signal when only the corresponding component exists with the target component, and the feature signal $F_i(t)$. The feature signal $F_i(t)$ used in obtaining the sole correlation value is the same as the feature signal $F_i(t)$ used in the correlation value calculating unit 62. As described above, the storage unit 63 stores therein a sole correlation value for each of the various wavelength shifts of the reference light.

When the sole correlation values are stored, the storage unit 63 preferably stores therein the sole correlation values resultant of subtracting the reference correlation values from the respective correlation values of the time when there is only one of the interference components with the target component, and of applying a correction for converting the sole correlation values into correlation values per unit concentration. The resultant correlation values are correlation values with the offsets included in the sole correlation values removal and being proportional to the concentrations of the target component and of the interference component. Therefore, it is possible to reduce the measurement errors. Note that a configuration not subtracting the reference correlation values is also possible.

The wavelength shift determining unit 66 determines the wavelength shift amount W of the reference light, from a light intensity signal that is an output signal of the photodetector 3.

As a method of determining the wavelength shift amount W, for example, the following sequence (a) or (b) is possible.

(a) The wavelength shift amount W is determined by obtaining sole correlation values $s_{itar}$ $(w_k)$ and $s_{iint}$ $(w_k)$ corresponding the target component and of the interference component, respectively, with the feature signal $F_i(t)$, using each of the wavelength shift $w_k$ (k=1, 2, . . . , 1) in the reference light, in advance, and by comparing and matching the sample correlation value collected at the time of measurement with these sole correlation values. In the case of this method, the required number of feature signals is equal to or more than the number obtained by adding one to the sum of the number of types of the target component and the number of types of the interference component. The reason for adding 1 is to accommodate with a wavelength shift amount that is a parameter common across the light absorption spectra of the respective components.

(b) The wavelength shift amount W of the reference light is determined using the relationship data indicating the relationship between ambient temperatures and the wavelength shift amounts W, and also using the measured ambient temperature.

At this time, the relationship data is generated in advance by obtaining the wavelength shift W of the reference light for each ambient temperature of the light source 2, through an experiment or a calculation.

The concentration calculating unit 65 calculates the concentration of the target component using a sample correlation value obtained by the correlation value calculating unit 62.

Specifically, the concentration calculating unit 65 calculates the concentration of the target component based on the sample correlation values obtained by the correlation value calculating unit 62, the wavelength shift amount W determined by the wavelength shift determining unit 66, and the sole correlation values stored in the storage unit 63. More specifically, the concentration calculating unit 65 corrects the sole correlation values stored in the storage unit 63 to obtain the corrected sole correlation values based on the wavelength shift amount W obtained by the wavelength shift determining unit 66. The concentration calculating unit 65 then calculates the concentration of the target component by solving the simultaneous equations including the sample correlation values obtained by the correlation value calculating unit 62, the corrected sole correlation values corresponding to the determined wavelength shift amount W, and the concentrations of the target component and of the respective interference components (see FIG. 5).

An example of an operation of the analysis device 100 will now be explained, also as a detailed description of each of the units. Hereinafter, it is assumed Unit sample gas contains one target component and one interference component.

< Reference Measurement>

To begin with, the light source control unit 5 controls the semiconductor laser 2 to modulate the wavelength of the laser light using a predetermined modulation frequency and modulation depth, around the peak of the absorption spectrum of the target component. Before carrying out the reference measurement using a span gas, the reference measurement using a zero gas may be performed to measure the reference correlation values.

A span gas (gas the component concentrations of which are known) is introduced into the cell 1 by an operator or automatically, and reference measurement is carried out. The reference measurements are collected using a span gas only containing the target component, and a span gas only containing the interference component.

Specifically, in the reference measurement, the logarithmic operation unit 61 receives output signals from the photodetector 3, the output signal corresponding to the respective wavelength shift amounts W of the reference light, and calculates the logarithmic intensities $L(t)$. The correlation value calculating unit 62 then calculates a correlation value between each of the logarithmic intensities $L(t)$ and each of the three feature signals $F_1(t)$, $F_2(t)$, and $F_3(t)$. The correlation value calculating unit 62 then subtracts the reference correlation values from the respective correlation values, and divides each of the result by the corresponding span gas concentration to calculate a sole correlation value that is a correlation values per unit concentration of the corresponding span gas. Instead of calculating the sole correlation value, the relationship between a span gas concentration and the correlation value for the span gas may be stored.

Specifically, this is done in the manner described below.

By adjusting the wavelength shift amount of the reference light to $w_k$ and introducing the span gas only containing the target component into the cell 1, the correlation value calculating unit 62 calculates the correlation values $S_{1tar}(w_k)$, $S_{2tar}(w_k)$, and $S_{3trar}(w_k)$ of the target component. $S_{1tar}(w_k)$ herein is a correlation value with the first feature signal, $S_{2tar}(w_k)$ is a correlation value with the second feature signal, and $S_{3tar}(w_k)$ is a correlation value with the third feature signal. The correlation value calculating unit 62 then calculates the sole correlation values $s_{1tar}(w_k)$, $s_{2tar}(w_k)$, and $s_{2tar}(w_k)$ by dividing the values resultant of subtracting the reference correlation value $R_i$ from each of the correlation values $S_{1tar}(w_k)$, $S_{2tar}(w_k)$, and $S_{3tar}(w_k)$, by the span gas concentration $c_{tar}$ of the target component. This procedure is performed at each wavelength shift amount while sequentially changing the wavelength shift amount of the reference light (every 0.001 cm$^{-1}$ between −0.01 cm$^{-1}$ to 0.01 cm$^{-1}$) using a method such as changing the temperature setting of the semiconductor laser 2, and the resultant relationships between the sole correlation values at the wavelength shift amount and that wavelength amount is stored. The span gas concentration $c_{tar}$ of the target component is input to the signal processing unit 6 by a user or the like in advance.

The correlation value calculating unit 62 calculates correlation values $S_{1int}(w_k)$, $S_{2int}(w_k)$, and $S_{3int}(w_k)$ for the interference component by adjusting the wavelength shift amount of the reference light to $w_k$, and introducing the span gas only containing the interference component into the cell 1. $S_{1int}(w_k)$ is herein a correlation value with the first feature signal, $S_{2int}(w_k)$ is a correlation value with the second feature signal, and $S_{3int}(w_k)$ is a correlation value with the third feature signal. The correlation value calculating unit 62 then calculates the sole correlation values $s_{1int}(w_k)$, $s_{2int}(w_k)$, and $s_{3int}(w_k)$ by dividing the values resultant of subtracting the reference correlation value $R_i$ from each of the correlation values $S_{1int}(w_k)$, $S_{2int}(w_k)$, and $S_{3int}(w_k)$, by the span gas concentration $c_{int}$ of the interference component. This procedure is performed in each wavelength shift amount while sequentially changing the wavelength shift amount of the reference light (every 0.001 cm$^{-1}$ between −0.01 cm$^{-1}$ to +0.01 cm$^{-1}$) using a method such as changing the temperature setting of the semiconductor laser 2. and the resultant relationship between the sole correlation values at the wavelength shift amount and the wavelength shift amount is stored. The span gas concentration $c_{int}$ of the interference component is input to the signal processing unit 6 by a user or the like in advance.

The sole correlation values $s_{1tar}(w_k)$, $s_{2tar}(w_k)$, $s_{3tar}(w_k)$, $s_{1int}(w_k)$, $s_{2int}(w_k)$, and $s_{3int}(w_k)$ calculated with each of the wavelength shift amounts $w_k$ of the reference light as described above are then stored in the storage unit 63. The reference measurement may be performed before the shipment of the product, or may be performed regularly.

<Sample Measurement>

The light source control unit 5 controls the semiconductor laser 2 to modulate the wavelength of the laser light using a predetermined modulation frequency and modulation depth, around the peak of the absorption spectrum of the target component. A sample gas is introduced into the cell 1 by an operator or automatically, and sample measurement is then carried out.

Specifically, in the sample measurement, the logarithmic operation unit 61 receives the output signal from the photodetector 3, and calculates the logarithmic intensity L(t). The correlation value calculating unit 62 then calculates sample correlation values $S_1$, $S_2$, and $S_3$ between the logarithmic intensities L(t) and the feature signals $F_1(t)$, $F_2(tt)$, and $F_3(t)$, respectively, and calculates sample correlation values $S'_1$. $S'_2$ obtained by subtracting the reference correlation values $R_i$ from the calculated sample correlation values, respectively.

In addition, the wavelength shill determining unit 66 determines the wavelength shift amount W with the method described above.

The concentration calculating unit 65 determines the corrected sole correlation values $s'_{1tar}$, $s'_{2tar}$, $s'_{1int}$, and $s'_{2int}$ corresponding to the target component and the interference component, being corrected using the sole correlation values with each wavelength shift amount $w_k$ of the reference light, the sole correlation values being stored in the storage unit 63, and the wavelength shift amount W determined by the wavelength shift determining unit 64. As a determination method, for example, a method using linear interpolation, or quadratic interpolation, spline interpolation, for example, is possible.

The concentration calculating unit 65 then solves the following binary simultaneous equations including the sample correlation values $S'_1$, $S'_2$ corrected with the reference correlation value calculated by the correlation value calculating unit 62, the corrected sole correlation values $s'_{1tar}$, $s'_{2tar}$, $s'_{1int}$, and $s'_{2int}$ and the concentrations $C_{tar}$ and $C_{int}$ of the target component and each of the interference components, in the same manner as in the first embodiment.

$$s'_{1tar} \cdot C_{tar} + s'_{1int} \cdot C_{int} = S'_1$$

$$s'_{2tar} \cdot C_{tar} + s'_{2int} \cdot C_{int} = S'_2 \quad \text{[Equation 8]}$$

Note that, when there are n types of gases including the target component and the interference component, the concentration calculating unit 65 solves the simultaneous equations with n unknowns, e.g. the equation indicated above (Equation 6), in the same manner as in the first embodiment.

According to the analysis device 100 according to the present embodiment configured as described above, the wavelength shift amount W of the reference light is determined, and the corrected concentration of the target component, with the effect of the wavelength shift of the reference light corrected, is calculated using the determined wavelength shift amount W. Therefore, it is possible to correct the change in the light absorption spectrum of the target component caused by the wavelength shift of the reference light, and to measure the concentration of the target component accurately.

Other Embodiments

For example, the configuration according to the first embodiment may be combined with the configuration according to the second embodiment to achieve an analysis device correcting both of the coexistent effect and the wavelength shift. Specifically, the analysis device 100 includes the broadening factor determining unit 64 according to the first embodiment and the wavelength shift determining unit 66 according to the second embodiment, and the storage unit 63 stores therein the sole correlation values $s_{ij}$ ($p_k$, $w_k$) for the pressure $p_k$ in each of various cells and the wavelength shift $w_k$ of the reference light, as disclosed in the first embodiment and the second embodiment, respectively.

In the analysis device 100, the concentration calculating unit 65 determines the corrected sole correlation values for the target component and the interference component, being corrected with the pressure in the cell, the broadening factor, and the wavelength shift amount, based on the following equation (Equation 9), using the pressure value p in the cell measured by the pressure sensor 7 and the broadening factor $F_B$ determined by the broadening factor determining unit 64, and the wavelength shift amount W determined by the wavelength shift determining unit 66. The concentration calculating unit 65 then calculates the concentration of the target component using (Equation 6) described above, using the corrected sole correlation values.

$$s'_{ij} = \frac{s_{ij}(F_B \cdot p, W)}{F_B} \quad \text{[Equation 9]}$$

The logarithmic operation unit 61 according to each of the embodiments described above performs a logarithmic operation of the light intensity signal of the photodetector 3, but may also calculate the logarithm of a ratio between the intensity of the sample light and the intensity of a modulated light that is the reference light (what is called absorbance) using the light intensity signal of the photodetector 3. At this time, the logarithmic operation unit 61 may calculate the absorbance by calculating the logarithm of the intensity of the sample light, calculating the logarithm of the intensity of the reference light, and then subtracting the latter from the former, or may calculate the absorbance by obtaining a ratio between the intensity of the sample light and the intensity of the reference light, and then taking the logarithm thereof.

In addition, the correlation value calculating unit 62 according to each of the embodiments described above calculates a correlation value between the intensity-related signal and each of the feature signals, but may calculate an inner product of the intensity-related signal and each of the feature signals.

In each of the embodiments described above, the storage unit 63 stores therein the sole correlation value corrected using the reference correlation value. Alternatively, the storage unit 63 may store therein an uncorrected sole correlation value, and the concentration calculating unit 63 may obtain the corrected sole correlation value by subtracting the reference correlation value from the uncorrected sole correlation value and converting the result to a per unit concentration.

The feature signals is not limited to the above embodiment, and may be any functions that are different from one another. In addition, for example, it is also possible to use a function indicating a waveform (sample spectrum) of light intensity, a logarithmic intensity, or an absorbance obtained by sending a span gas having a known concentration, as a feature signal. In order to measure the concentration of one target component, it will be sufficient if there is at least one feature signal.

Furthermore, when there are n types of gas, including the target component and the interference component, it is possible to obtain sole correlation values and sample correlation values in a number greater titan the number of the types of gas, using feature signals the number of types of which is greater than n, to create simultaneous equations having elements greater in number than the number of gas types, and to determine the concentration of each component using the least squares method. In this manner, it is possible to determine the concentration with a smaller error even for a measurement noise.

In the first embodiment, the sole correlation values at the pressure in each of the cells are stored in the storage unit 63 during the reference measurement, and converted into the sole correlation values included in the corresponding broadening factor using the relationship of the equation (Equation 2). However, the sole correlation value included in each of the broadening factors may be measured directly at the time of reference measurement, and stored in the storage unit 63.

Figure 8:
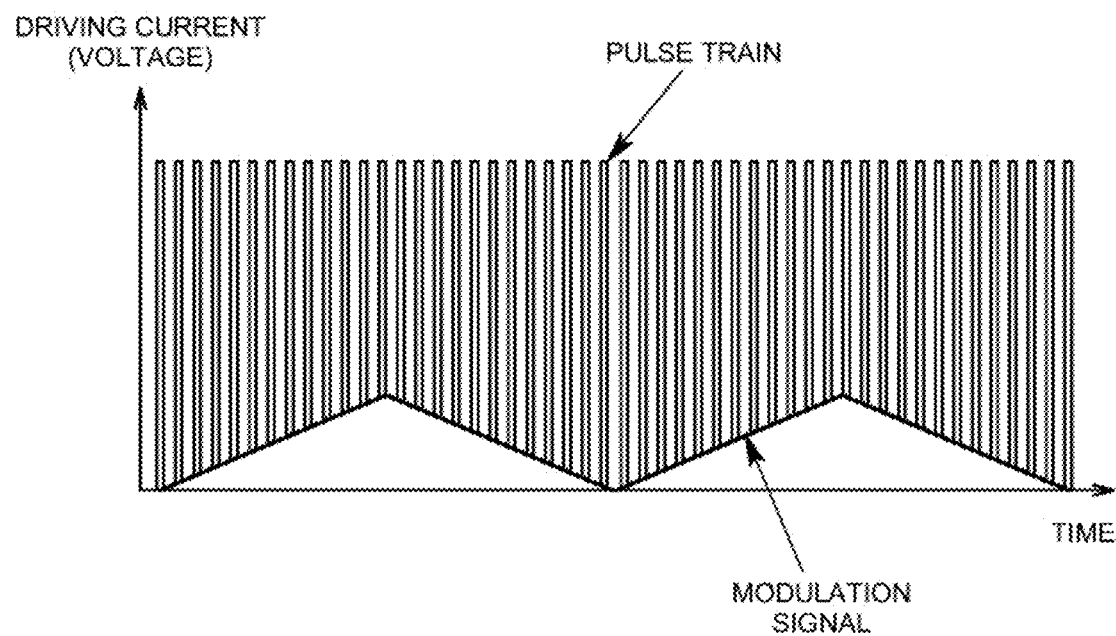
FIG. 8 is a diagram illustrating a driving current (voltage) and a modulation signal in pseudo continuous oscillation.

The light source control unit 5 according to each of the above embodiments causes the semiconductor laser to perform continuous oscillation (CW), but may perform pseudo continuous oscillation (pseudo CW) as illustrated in FIG. 8. In such a case, the light source control unit 5 controls the current source (or voltage source) of each semiconductor laser 2 by outputting a current (or voltage) control signal to set the driving current (driving voltage) of the current source (or voltage source) to a predetermined threshold or higher, to cause the driving current to oscillate. Specifically, the light source control unit 5 performs pseudo continuous oscillation by oscillating a pulse having a predetermined pulse width (for example, 10 to 50 ns at a duty ratio of 5%) repeated at a predetermined cycle (for example, at a cycle of 1 to 5 MHz). The light source control unit 5 then changes the driving current (driving voltage) of the current source tor voltage source) at a value for wavelength sweeping that is less than the threshold value for pulse oscillation at a predetermined frequency to generate a temperature change and sweep the oscillation wavelength of the laser light. As examples of the modulation signal for modulating the driving current, the signal changes in a triangular wave shape, a sawtooth wave shape, or a sine wave shape, and has a frequency of 1 to 100 Hz, for example.

Figure 9:
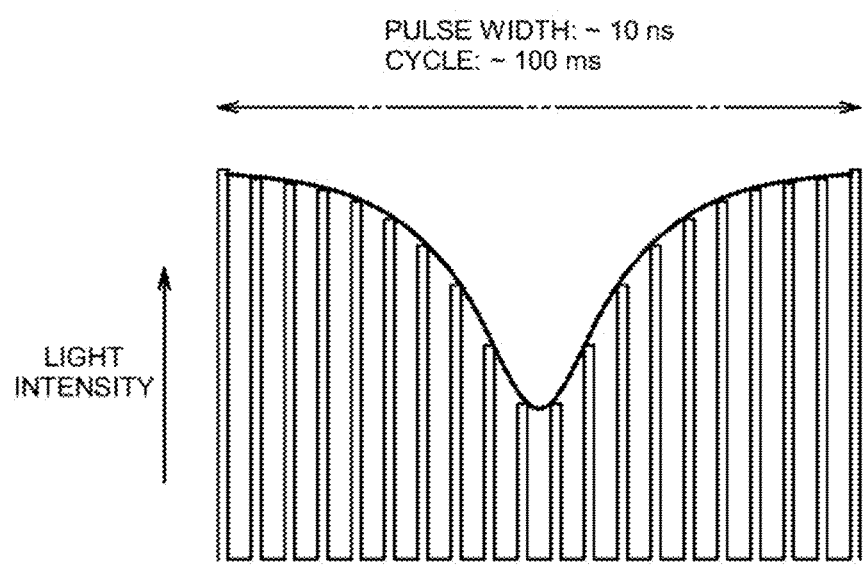
FIG. 9 is a schematic diagram illustrating a measurement principle using pseudo continuous oscillation.
Figure 10:
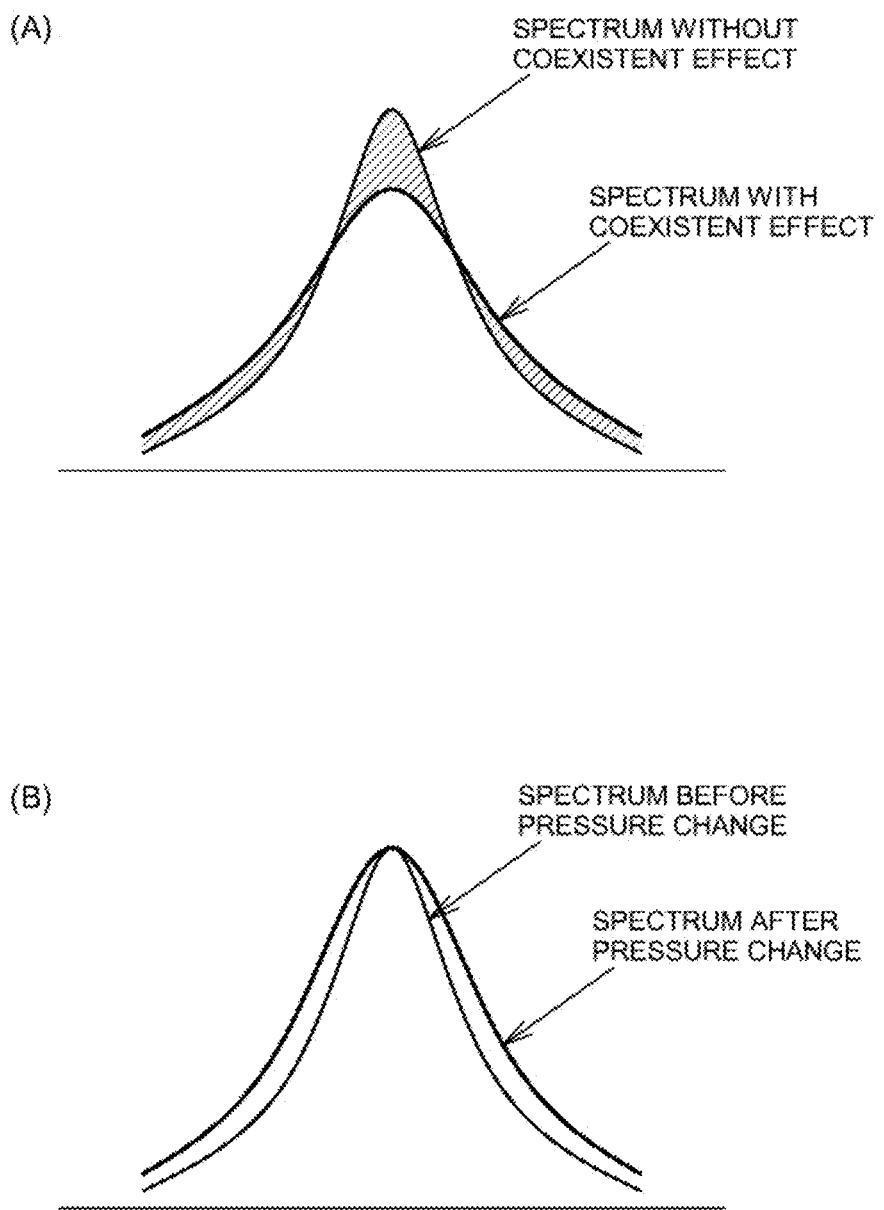
FIG. 10 is a schematic diagram illustrating a spectrum change cause by coexistent effect and a spectrum change caused by a pressure change.

FIG. 9 illustrates an example of the light intensity signal obtained by the photodetector by causing the semiconductor laser to perform pseudo continuous oscillation in the manner described above. In this manner, the absorption spectrum can be obtained over the entire pulse train. With the pseudo continuous oscillation, the light source consumes less power than that in the continuous oscillation, the exhaust heat treatment becomes easier, and the life of the light source can be extended.

The sample gas may also be the atmosphere, as well as exhaust gas, or may be a liquid or a solid. In this sense, the present invention can be applied to not only a gas but also to a liquid or a solid as a target component. Furthermore, the present invention may be used not only for the absorbance of the light passed through the measurement target, but also for the absorbance calculation of reflection.

The light source may be another type of laser, regardless of the semiconductor laser, or any light source may be used as long as the light source is a single-wavelength light source having a half width sufficient to ensure the measurement accuracy, and can perform wavelength modulation.

In addition, various modifications and combinations of the embodiments may be made within the scope not deviating from the gist of the present invention.

INDUSTRIAL APPLICABILITY

According to the present invention, the concentration of the target component can be accurately measured by correcting the change in the light absorption spectrum of the target component caused by the coexistent effect of the coexisting component or the wavelength shift of the reference light.

The invention claimed is:

1. An analysis device that analyzes a target component included in a sample including one or more interference components, the analysis device comprising:
    a light source that irradiates the sample with reference light;
    a photodetector that detects an intensity of sample light that is the reference light having transmitted through the sample;
    a parameter determining unit that determines a parameter representing a change in a light absorption spectrum of the target component or a change in a light absorption spectrum of an interference component, the change being caused by a coexisting component included in the sample or by a wavelength shift of the reference light;
    a concentration calculating unit that calculates a corrected concentration of the target component, from an intensity-related signal related to the intensity of the sample light, by using the parameter representing the change in the light absorption spectrum;
    a correlation value calculating unit that calculates a correlation value between the intensity-related signal related to the intensity of the sample light and a predetermined feature signal, and that calculates a plurality of correlation values using a number of feature signals equal to or more than a sum of a number of types of the target component and a number of types of the interference component; and
    a storage unit that stores a sole correlation value that is a correlation value between a per unit concentration of the target component and a per unit concentration of each of the one or more interference components, the sole correlation value being obtained from the intensity-related signal when only the corresponding interference component exists with the target component, and from the number of feature signals, wherein
    the concentration calculating unit calculates a corrected concentration of the target component, the corrected concentration being corrected for a coexistent effect of the coexisting component or for the wavelength shift of the reference light, using a plurality of correlation values obtained by the correlation value calculating unit, a plurality of the sole correlation values, and the parameter representing the change in the light absorption spectrum of the target component or the changes in the one or more interference components.

2. The analysis device according to claim 1, wherein the parameter representing the change in the light absorption spectrum is a broadening factor or a wavelength shift amount of the reference light, the broadening factor representing a rate of the change in the light absorption spectrum of the target component or the change in the light absorption spectrum of the interference component, the change being caused by the coexisting component included in the sample.

3. The analysis device according to claim 2, wherein the concentration calculating unit calculates a corrected concentration of the target component, by correcting the coexistent effect of the coexisting component or the wavelength shift of the reference light, using the intensity-related signal related to the intensity of the sample light, and the broadening factor or the wavelength shift amount.

4. The analysis device according to claim 2, wherein the parameter determining unit determines the broadening factor by fitting reference data to sample data, the reference data being data related to light absorption signals of the target component and of the interference component the broadening factor of which or a pressure of which is known, and the sample data being data related to a light absorption signal obtained from the intensity of the sample light.

5. The analysis device according to claim 2, wherein the parameter determining unit determines the broadening factor by using relationship data indicating a relationship between concentrations of the coexisting component and the broadening factor, and a measured concentration of the coexisting component.

6. The analysis device according to claim 2, wherein the parameter determining unit determines a wavelength shift amount by fitting reference data to sample data, the reference data being data related to light absorption signals of the target component and of the interference component for which a wavelength shift amount is known, and the sample data being data related to a light absorption signal obtained from the intensity of the sample light.

7. The analysis device according to claim 2, wherein the parameter determining unit determines the wavelength shift amount of the reference light by using relationship data indicating a relationship between ambient temperatures and wavelength shift amounts, and a measured ambient temperature.

8. The analysis device according to claim 1, wherein the concentration calculating unit corrects the plurality of sole correlation values by using the parameter representing the change in the light absorption spectrum of the target component or the change in the light absorption spectrum of the interference component, and calculates the concentration of the target component by using the plurality of corrected sole correlation values and the plurality of correlation values obtained by the correlation value calculating unit.

9. The analysis device according to claim 8, wherein the concentration calculating unit calculates the concentration of the target component by solving simultaneous equations including the plurality of correlation values obtained by the correlation value calculating unit, the plurality of corrected sole correlation values, and the concentrations of the target component and each of the interference components.

10. The analysis device according to claim 2, further comprising a pressure sensor that monitors a pressure of the sample, wherein the concentration calculating unit corrects the sole correlation value using a pressure value obtained by the pressure sensor.

11. The analysis device according to claim 10, wherein the concentration calculating unit corrects the sole correlation value by using the sole correlation values of each of the components, the sole correlation values being obtained for each of a plurality of known pressures of the sample, the plurality of correlation values obtained by the correlation value calculating unit, the pressure value inside a cell, and a relationship represented by following equation (Equation 2), $$s'_{ij} = \frac{s_{ij}(F_B \cdot p)}{F_B} \quad \text{[Equation 2]}$$

where, p denotes the pressure of the sample measured by the pressure sensor; FB denotes the broadening factor; $S_{ij}$ denotes a sole correlation value corresponding to each of the pressures stored in the storage unit, and $s'_{ij}$ denotes a corrected sole correlation values, and the equation (Equation 2) indicates that the corrected sole correlation value $s'_{ij}$ is obtained, for a sole correlation value $s_{ij}(p)$ with a sample pressure p at time of a sample measurement, by multiplying 1/FB to the sole correlation value resultant of multiplying the pressure by FB.

12. A non-transitory computer readable medium storing a program applied to an analysis device that includes a light source that irradiates a sample, including one or more interference components, with reference light, and a photodetector that detects sample light having transmitted through the sample, the program causing the analysis device to implement functions as:

a parameter determining unit that determines a parameter representing a change in a light absorption spectrum of a target component or a change in a light absorption spectrum of an interference component, the change being caused by a coexisting component included in the sample or by a wavelength shift of the reference light;

a concentration calculating unit that calculates a corrected concentration of the target component, from an intensity-related signal related to an intensity of the sample light, by using the parameter representing the change in the light absorption spectrum;

a correlation value calculating unit that calculates a correlation value between the intensity-related signal related to the intensity of the sample light and a predetermined feature signal, and that calculates a plurality of correlation values using a number of feature signals equal to or more than a sum of a number of types of the target component and a number of types of the interference component; and a storage unit that stores a sole correlation value that is a correlation value between a per unit concentration of the target component and a per unit concentration of each of the one or more interference components, the sole correlation value being obtained from the intensity-related signal when only the corresponding interference component exists with the target component, and from the number of feature signals, wherein the concentration calculating unit calculates a corrected concentration of the target component, the corrected concentration being corrected for a coexistent effect of the coexisting component or for the wavelength shift of the reference light, using a plurality of correlation values obtained by the correlation value calculating unit, a plurality of the sole correlation values, and the parameter representing the change in the light absorption spectrum of the target component or the changes in the one or more interference components.

13. An analysis method for analyzing a target component included in a sample including one or more interference components, by using a light source that irradiates the sample with reference light, and a photodetector that detects sample light having transmitted through the sample, the analysis method comprising:

determining a parameter representing a change in a light absorption spectrum of the target component or a change in a light absorption spectrum of an interference component, the change being caused by a coexisting component included in the sample or by a wavelength shift of the reference light;

calculating a corrected concentration of the target component, from an intensity-related signal related to an intensity of the sample light, by using the parameter representing the change in the light absorption spectrum;

calculating a correlation value between the intensity-related signal related to the intensity of the sample light and a predetermined feature signal;

calculating a plurality of correlation values using a number of feature signals equal to or more than a sum of a number of types of the target component and a number of types of the interference component;

storing a sole correlation value that is a correlation value between a per unit concentration of the target component and a per unit concentration of each of the one or more interference components, the sole correlation value being obtained from the intensity-related signal when only the corresponding interference component exists with the target component, and from the number of feature signals; and calculating a corrected concentration of the target component, the corrected concentration being corrected for a coexistent effect of the coexisting component or for the wavelength shift of the reference light, using a plurality of correlation values obtained by the correlation value calculating unit, a plurality of the sole correlation values, and the parameter representing the change in the light absorption spectrum of the target component or the changes in the interference components.

* * * * *